United States Patent [19]

Alker et al.

[11] Patent Number: 4,892,881

[45] Date of Patent: Jan. 9, 1990

[54] DIHYDROPYRIDINE ANTI-ISCHAEMIC AND ANTIHYPERTENSIVE AGENTS

[75] Inventors: David Alker, Margate; Simon F. Campbell, Kingsdown; Peter E. Cross, Canterbury, all of England

[73] Assignee: Pfizer Inc., New York, N.Y.

[21] Appl. No.: 115,274

[22] Filed: Nov. 2, 1987

Related U.S. Application Data

[62] Division of Ser. No. 927,881, Nov. 5, 1986, Pat. No. 4,732,985.

[30] Foreign Application Priority Data

Nov. 9, 1985 [GB] United Kingdom ............... 8527698

[51] Int. Cl.$^4$ .................. A61K 31/455; C07D 211/90
[52] U.S. Cl. ...................................... 514/356; 514/272; 514/274; 514/332; 514/340; 514/341; 546/276; 546/278; 546/263; 546/321; 544/310; 544/321; 544/316
[58] Field of Search ............ 544/310, 316, 321; 546/276, 278, 263, 321; 514/272, 274, 332, 340, 341, 356

[56] References Cited

FOREIGN PATENT DOCUMENTS

WO87/00836 2/1987 PCT Int'l Appl. ............... 546/321

Primary Examiner—Jane T. Fan

Attorney, Agent, or Firm—Peter C. Richardson; J. Trevor Lumb; James M. McManus

[57] ABSTRACT

1,4-Dihydropyridine anti-ischaemic and antihypertensive agent of the formula:

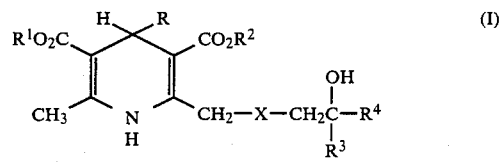

or a pharmaceutically acceptable salt thereof, wherein R is 2-chlorophenyl, 2,3-dichlorophenyl or 2-chloro-3-trifluoromethylphenyl;

$R^1$ and $R^2$ are each independently $C_1$–$C_4$ alkyl;

X is O or S;

$R^3$ is H or $C_1$–$C_4$ alkyl; and $R^4$ is 1,2,4-triazol-1-ylmethyl, imidazol-1-ylmethyl, azidomethyl, 2,4,5-trimethylimidazol-1-ylmethyl, 3,4-dihydro-4-oxopyrimidin-2-ylthiomethyl, pyrimidin-2-ylthiomethyl; pyrimidin-2-ylaminomethyl, 3,4-dihydro-4-oxopyrimidin-2-ylaminomethyl, 2-aminopyrimidin-4-yloxymethyl, methoxymethyl, 2-furyl, 2-pyridylmethyl, imidazol-2-yl, hydroxymethyl, aminomethyl, 1,2,4-triazol-4-ylmethyl or 2-hydroxyethyl, and intermediates leading thereto.

7 Claims, No Drawings

4,892,881

DIHYDROPYRIDINE ANTI-ISCHAEMIC AND ANTIHYPERTENSIVE AGENTS

This application is a divisional application of copending application Ser. No. 927,881, filed Nov. 5, 1986 now U.S. Pat. No. 4,732,985 issued 3/22/88.

BACKGROUND OF THE INVENTION

This invention relates to certain dihydropyridines, specifically to certain 1,4-dihydropyridines having a hydroxy-substituted alkylene group as part of a side chain attached to the 2-position, and which have utility as anti-ischaemic and antihypertensive agents.

These dihydropyridines reduce the movement of calcium into the cell and they are thus able to delay or prevent the cardiac contracture which is believed to be caused by an accumulation of intracellular calcium under ischaemic conditions. Excessive calcium influx during ischaemia can have a number of additional adverse effects which would further compromise the ischaemic myocardium. These include less efficient use of oxygen for ATP production, activation of mitochondrial fatty acid oxidation and possibly, promotion of cell necrosis. Thus the compounds are useful in the treatment or prevention of a variety of cardiac conditions, such as angina pectoris, cardiac arrhythmias, heart attacks and cardiac hypertrophy. The compounds also have vasodilator activity since they can inhibit calcium influx in cells of vascular tissue and they are thus also useful as antihypertensive agents and for the treatment of coronary vasospasm.

SUMMARY OF THE INVENTION

Thus the present invention provides compounds of the formula:

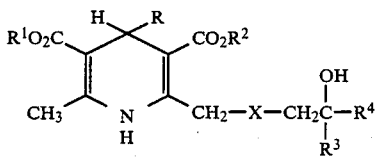

(I)

or a pharmaceutically acceptable acid addition salt thereof wherein

R is 2-chlorophenyl, 2,3-dichlorophenyl or 2-chloro-3-trifluoromethylphenyl;

$R^1$ and $R^2$ are each independently $C_1$–$C_4$ alkyl; X is O or S; $R^3$ is H or $C_1$–$C_4$ alkyl; and $R^4$ is 1,2,4-triazol-1-ylmethyl, imidazol-1-ylmethyl, azidomethyl, 2,4,5-trimethylimidazol-1-ylmethyl, 3,4-dihydro-4-oxopyrimidin-2-ylthiomethyl, pyrimidin-2-ylthiomethyl; pyrimidin-2-ylaminomethyl, 3,4-dihydro-4-oxopyrimidin-2-ylaminomethyl, 2-aminopyrimidin-4-yloxymethyl, methoxymethyl, 2-furyl, 2-pyridylmethyl, imidazol-2-yl, hydroxymethyl, aminomethyl, 1,2,4-triazol-4-ylmethyl or 2-hydroxyethyl.

Preferred are those compounds where $R^1$ and $R^2$ are each $C_1$–$C_4$ alkyl, $R^3$ is H, $R^4$ is hydroxymethyl and X is O. Especially preferred within this group of compounds are 1-{[4-(2,3-dichlorophenyl)-3-ethoxycarbonyl-5-methoxycarbonyl-6-methyl-1,4-dihydropyrid-2-yl]methoxy}-2,3-dihydroxypropane and 1-{[4-(2-chloro-3-trifluoromethylphenyl)-3-ethoxycarbonyl-5-methoxycarbonyl-6-methyl-1,4-dihydropyrid-2-yl]methoxy}-2,3-dihydroxypropane.

In addition to pharmaceutical compositions of the compounds of the present invention with pharmaceutically acceptable carriers or diluents, the present invention also is comprised of methods for treating hypertension and ischaemia.

Useful as intermediates leading to the compounds of the instant invention are intermediates of the formula

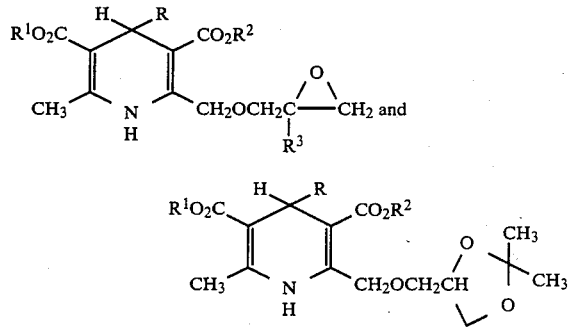

where R is 2-chlorophenyl, 2,3-dichlorophenyl or 2-chloro-3-trifluoromethylphenyl; $R^1$ and $R^2$ are each $C_1$–$C_4$ alkyl; and $R^3$ is H or $C_1$–$C_4$ alkyl.

When keto-enol tautomerism occurs both tautomers, of course, are within the scope of the invention. For example, tautomerism occurs in the case of the 3,4-dihydro-4-oxopyrimidin-2-yl group, i.e.:

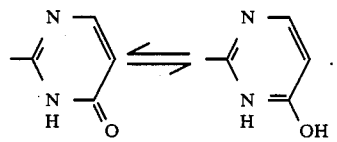

Which particular isomer is present in normal circumstances can be readily determined by appropriate physical measurements, e.g. by infra-red spectroscopy, and, in some instances, the compound may exist as mixtures of the two forms.

The pharmaceutically acceptable acid addition salts of the compounds of the formula (I) which form such salts are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate and tartrate salts. For some compounds, salts may also be formed with bases, examples are the sodium, potassium and ammonium salts.

The term "halo" means fluoro, chloro, bromo or iodo. Alkyl and alkoxy groups having 3 or more carbon atoms can be straight or branched chain. Compounds containing asymmetric centres will exist as one or more pairs of enantiomers and the invention includes the separated d- and l- optically active isomers as well as mixtures thereof.

DETAILED DESCRIPTION OF THE INVENTION

The compounds of the forumula (I) can be prepared by a number of routes, including the following:

(1) The first route, which prepares certain of the compounds of the formula (I) in which X is O or S, these being designated (IA), involved a nucleophilic displacement reaction on an oxirane as follows:

(2) This route to the compounds designated (IB) involves the reaction of a lithio compound with a ketone ($R^3 = C_1-C_4$ alkyl only), as follows:

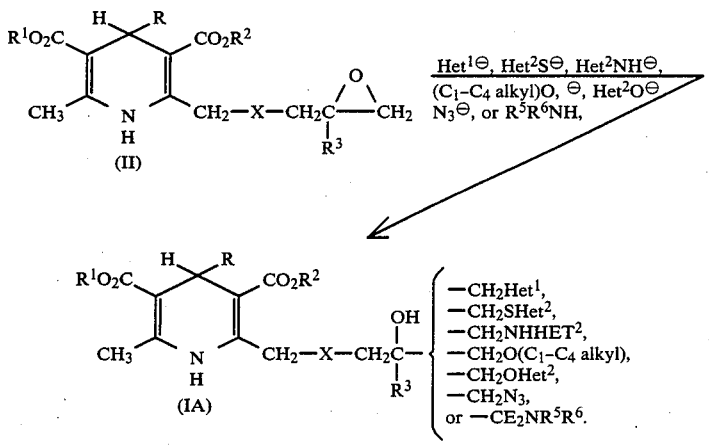

$R$, $R^1$, $R^2$ and $R^3$ are as defined for formula (I) and X is O or S. $Het^1$ and $Het^2$ are various heterocyclic groups.

The nucleophile is typically the sodium or potassium salt generated by the reaction of the appropriate heterocycle, heterocyclic thiol, heterocyclic amine, etc.; with an appropriate base. The base is chosen having regard to the lability of the proton to be removed as will be known to those skilled in the art. Often sodium hydride or sodium carbonate are suitable. In the case of the preparation of the compounds in which $R^4$ is $-CH_2NR^5R^6$, generally reaction with $R^5R_6NH$ will proceed satisfactorily, i.e. an additional base is not essential. Catalysts can be used to speed up the reaction. For example, in the case of the formation of the azides, the reaction is typically carried out using sodium azide in the presence of a magnesium perchlorate catalyst. In some cases the presence of a Crown ether may assist in solubilising the reagents. The process is typically carried out at room temperature in an appropriate organic solvent such as tetrahydrofuran, dimethylformamide, ethanol or aqueous dioxane, as appropriate. Also, if necessary the reaction mixture can be heated at up to, say, 100° C. in order to accelerate the reaction. The product can then be isolated and purified by conventional techniques such as solvent extraction/chromatography on silica.

The oxiranes of the formula (II) are available by conventional techniques such as those described in Preparations 1 and 2 hereinafter, or analogously thereto. Preparations 6, 7 and 10 describe the preparation of the methyl ketone starting material used in Preparation 1. The method of Preparation 10 is applicable not only to the preparation of the methyl ketones but also to the higher alkyl ketones via either a $C_1-C_4$ alkylmagnesium bromide or a $C_1-C_4$ alkyllithium. Although an imidazolide is used in Preparation 10 acid chlorides and anhydrides are also suitable. The acid used in Preparation 10 is described in European patent application publication no. 0100189 and analogous compounds can be prepared similarly. The diol starting material used to obtain the oxirane of Preparation 2, which is also a compound of the invention, can be prepared as described in the sequential steps of Preparations 5 and 3 and Example 20. Other diols can be prepared analogously. When X is S a useful route to the diols is described in Example 23.

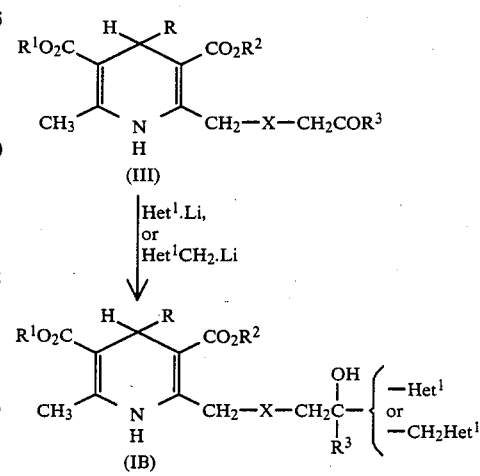

Again $R$, $R^1$, $R^2$ and $R^3$ are as defined for formula (I) and X is O or S. $Het^1$ is a heterocyclic group.

The lithio derivatives can be generated conventionally by the reaction of n-butyllithium with the appropriate aryl or heterocyclic compound at low temperature ($-78°$ to about 0° C.) in an organic solvent such as tetrahydrofuran. In some cases it may be necessary to use an N-protected heterocycle such as 1-diethoxymethylimidazole: see Example 15. The protecting group can be removed conventionally. In a typical procedure a solution of the ketone (III) in a solvent such as tetrahydrofuran is added to the solution of the lithio compound and the resulting mixture is stirred with ice cooling for, say, 1-2 hours and then allowed to warm to room temperature. Again the product can be isolated and purified conventionally.

(3) Reaction of the oxiranes (II) with a $C_1-C_5$ alkanoic acid in the presence of a small amount of a mineral acid yields the alkanoyloxy derivatives [$-CH_2XCH_2$-$C(OH)(R^3)CH_2O.(C_1-C_5$ alkanoyl)] which are then hydrolysed using aqueous base to yield the compounds of the formula (I) in which $R^4$ is $-CH_2OH$. Preferably the reaction is carried out by stirring a solution of the oxirane in acetic acid containing a few drops of a mineral acid such as concentrated sulphuric acid, followed by evaporation. The resulting residue is then dissolved in an organic solvent such as dioxane and treated with a base such as aqueous sodium hydroxide. The product can then be isolated and purified conventionally.

(4) The compounds of the formula (I) in which $R^4$ is —$CH_2NH_2$ are most conveniently prepared by the reduction of the corresponding azides according to conventional techniques, e.g. using Zn/aqueous HCl/methanol or $H_2$/Pd/$CaCO_3$/methanol or ethanol (see European patent applications publication nos. 0089167 and 0100189) or by using a reagent such as propane-1,3-dithiol in the presence of triethylamine and in a solvent such as methanol.

(5) Compounds in which $R^4$ is —$CH_2$—(1,2,4-triazol-4-yl) can be prepared by the conventional technique of reacting the corresponding compounds in which $R^4$ is —$CH_2NH_2$ with N,N-dimethylformamide azine. The reaction is typically carried out in the presence of a sulphonic acid such as para-toluenesulphonic acid and in a solvent such as toluene with heating at up to the reflux temperature.

(6) Compounds in which $R^3$ is H and $R^4$ is —$CH_2OH$ can also be prepared from the appropriate dioxolanes by treatment with an aqueous mineral or organic acid such as aqueous acetic acid. The reaction is typically carried out at room temperature. It can be illustrated as follows:

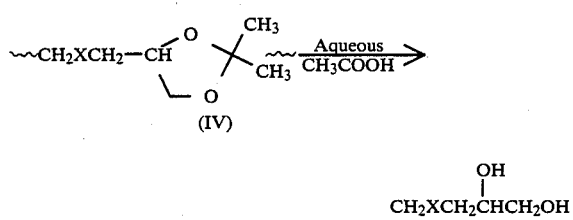

The dioxolanes are available by conventional techniques—see for example Preparations 3 to 5 hereinafter.

(7) Compounds of the formula (I) in which $R^3$ is H and $R^4$ is —$(CH_2)_2OH$ can be prepared by reduction of the appropriate ethyl acetoacetates (or the corresponding methyl, propyl or butyl derivatives) as follows:

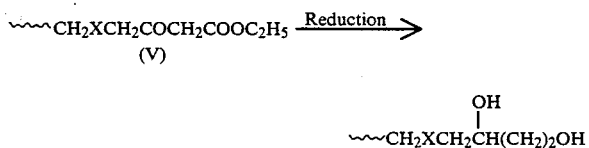

The reduction can be carried out according to conventional techniques, e.g. using lithium aluminum hydride in an organic solvent such as tetrahydrofuran, and typically with ice-cooling of the solution.

The acetoacetates are available according to conventional techniques such as those described in European patent application publication no. 0132375.

(8) The compounds in which X is S are also conveniently prepared by the reaction of the appropriate 2-bromomethyl 1,4-dihydropyridine with the appropriate thiol, as follows:

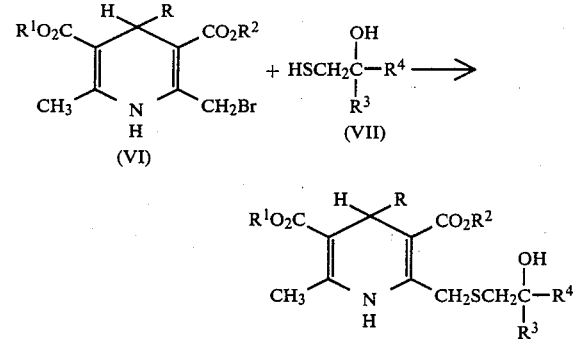

The reaction is typically carried out in the presence of a base such as potassium carbonate and in a solvent such as tetrahydrofuran, and generally the reaction will proceed in a satisfactory manner at room temperature. The 2-bromomethyl 1,4-dihydropyridines are known compounds.

(9) The compounds of the formula (I) in which p is 1 or 2, i.e., the sulphinyl and sulphonyl compounds, are most conveniently prepared by the oxidation of the corresponding thio compounds [formula (I), X=S], typically by using about one (sulphinyl) or two (sulphonyl) equivalents of a suitable oxidising agent such as metachloroperbenzoic acid or sodium metaperiodate.

The ability of the compounds to inhibit the movement of calcium into the cell is shown by their effectiveness in reducing the response of isolated vascular tissue to an increase in calcium ion concentration in vitro. The test is performed by mounting spirally cut strips of rat aorta with one end fixed and the other attached to a force transducer. The tissue is immersed in a bath of physiological saline solution containing potassium ions at a concentration of 45 millimolar and no calcium. Calcium chloride is added to the bath with a pipette to give a final calcium ion concentration of 2 millimolar. The change in tension caused by the resulting contraction of the tissue is noted. The bath is drained and replaced with fresh saline solution and after 45 minutes the procedure is repeated with the particular compound under test present in the saline solution. The concentration of compound required to reduce the response by 50% is recorded.

The antihypertensive activity of the compounds is also evaluated after oral administration by measuring the fall in blood pressure in spontaneously hypertensive rats or renally hypertensive dogs.

For administration to man in the curative or prophylactic treatment of cardiac conditions and hypertension, oral dosages of the compounds will generally be in the range of from 2–100 mg daily for an average adult patient (70 kg). Thus for a typical adult patient, individual tablets or capsules contain from 1 to 10 mg of active compound, in a suitable pharmaceutically acceptable vehicle or carrier. Dosages for intravenous administration would typically be within the range 1 to 10 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

Thus in a further aspect the invention provides a pharmaceutical composition comprising a compound of the formula (I), or a pharmaceutically acceptable salt thereof, together with a pharmaceutically acceptable diluent or carrier.

The invention also provides a compound of the formula (I) or a pharmaceutically acceptable salt thereof, for use as a medicament, particularly for use in the treatment of angina and hypertension.

The novel intermediates of the formulae (II) and (IV) also form a part of the invention.

The invention yet further provides the use of a compound of the formula (I) or of a pharmaceutically acceptable salt thereof for the manufacture of an anti-ischaemic or antihypertensive agent.

The preparation of the compounds of the formula (I) is illustrated by the following Examples.

EXAMPLE 1

1-{[4-(2,3-Dichlorophenyl)-3-ethoxycarbonyl-5-methoxycarbonyl-6-methyl-1,4-dihydropyrid-2-yl]methoxy}-2-hydroxy-2-methyl-3-(1,2,4-triazol-1-yl)propane

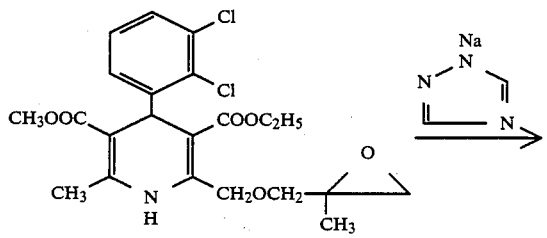

A mixture of 2-{[4-(2,3-dichlorophenyl)-3-ethoxycarbonyl-5-methoxycarbonyl-6-methyl-1,4-dihydropyrid-2-yl]methoxymethyl}-2-methyloxirane (0.80 g), 1,2,4-triazole sodium salt (0.60 g) and "18-Crown-6" (20 mg) in tetrahydrofuran (25 ml) was stirred at room temperature for two days and then partitioned between ethyl acetate and water. The layers were separated and the organic layer was washed with water, dried over $Na_2SO_4$ and evaporated. The residue was purified by chromatography on $SiO_2$ (12 g) using toluene plus 0-100% ethyl acetate as the eluant. Appropriate fractions were combined and evaporated and the residue was triturated with ether. The resulting solid was collected, washed with ether and dried to give the title compound (0.49 g), m.p. 149°-160° C.

Analysis %: Found: C, 53.69; H, 5.51; N, 10.15; $C_{24}H_{28}Cl_2N_4O_6$ requires: C, 53.43; H, 5.19; N, 10.39.

EXAMPLES 2-12

The following compounds were prepared similarly to the method described in Example 1 from either 2-{[4-(2,3-dichlorophenyl)-3-ethoxycarbonyl-5-methoxycarbonyl-6-methyl-1,4-dihydropyrid-2-yl]methoxymethyl}oxirane or 2-{[4-(2,3-dichlorophenyl)-3-ethoxycarbonyl-5-methoxycarbonyl-6-methyl-1,4-dihydropyrid-2-yl]methoxymethyl}-2-methyloxirane and the appropriate "reagents" as defined in each Example. In the case of the reaction of 2-{[4-(2,3-dichlorophenyl)-3-ethoxycarbonyl-5-methoxycarbonyl-6-methyl-1,4-dihydropyrid-2-yl]methoxymethyl}-2-methyloxirane with 2-amino-4-pyrimidone and potassium carbonate in aqueous dioxane two products were obtained (see Examples 10 and 11) and these were separated by chromatography. In Example 7 the product was characterised as a hemihydrate while in Example 9 the product was characterised as a hydrate. "THF" is tetrahydrofuran and "DMF" is N,N-dimethylformamide. Example 1 was the only Example carried out in the presence of a Crown ether.

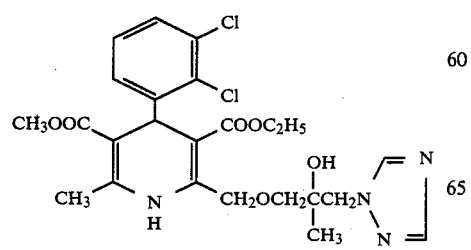

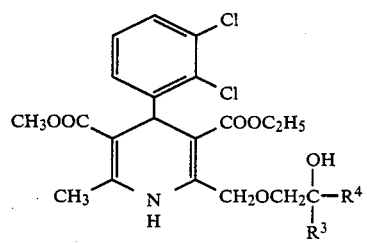

| Example | R³ | R⁴ | "Reagents" | m.p. (°C.) | Analysis % (Theoretical in Brackets) | | |
|---|---|---|---|---|---|---|---|
| | | | | | C | H | N |
| 2 | H | 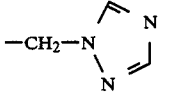 —CH₂—N(triazole) | 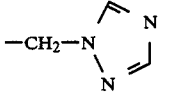 Na⊕N⊖(triazole), T.H.F. | 137–140 | 52.67 (52.57 | 5.09 4.95 | 10.39 10.67 |
| 3 | CH₃ | —CH₂—N(imidazole) | NaH/HN(imidazole), T.H.F. | 169–180 | 55.57 (55.76 | 5.46 5.39 | 7.71 7.81) |
| 4 | H | —CH₂—N₃ | NaN₃/Mg(ClO₄)₂, H₂O/dioxane. | Oil | Characterised by n.m.r. (see end of Table) | | |
| 5 | CH₃ | —CH₂—N₃ | NaN₃Mg(ClO₄)₃ H₂O/dioxane. | Oil | Characterised by n.m.r. (see end of Table) | | |
| 6 | CH₃ | —CH₂—N(trimethylimidazole) | NaH/HN(trimethylimidazole), T.H.F. | 175–180 (decomp) | 57.41 (57/93 | 6.20 6.03 | 7.10 7.24) |
| 7 | CH₃ | —CH₂—S-(2-mercapto-6-oxopyrimidine) | K₂CO₃/N(thiouracil), EtOH. | 120 | 51.40 (51.40 | 5.00 4.98 | 6.74 6.92) |
| 8 | CH₃ | —CH₂—S-(2-mercaptopyrimidine) | K₂CO₃/N(2-mercaptopyrimidine), EtOH. | 50–55 | 54.73 (53.61 | 5.33 5.02 | 6.69 7.21) |
| 9 | CH₃ | —CH₂—NH-(2-aminopyrimidine) | NaH/N(2-aminopyrimidine), DMF. | 60 | 52.57 (53.51 | 5.22 5.52 | 10.14 9.86) |
| 10 | CH₃ | —CH₂—NH-(2-amino-6-oxopyrimidine) | K₂CO₃/N(2-amino-6-oxopyrimidine), H₂O/dioxane. | 180–185 | 53.70 (53.70 | 5.31 5.20 | 9.44 9.64) |
| 11 | CH₃ | —CH₂—O-(2-aminopyrimidine) | | 168–172 | 53.41 (53.70 | 5.18 5.20 | 9.38 9.64) |
| 12 | CH₃ | —CH₂—OMe | K₂CO₃/MeOH. | foam | 54.52 (54.98 | 5.70 5.82 | 2.80 2.79) |

EXAMPLE 4

'H-n.m.r. (CDCl₃) δ=7.43 (1H, broad s), 6.9–7.4 (3H, m), 5.46 (1H, s), 4.74 (2H, s), 4.05 (2H, q, J=7 Hz), 3.9–4.2 (1H, m), 3.62 (3H, s), 3.57 (2H, AB system, J=5 Hz), 2.8–3.3 (2H, m), 2.31 (3H, s) and 1.17 (3H, t, J=7 Hz).

EXAMPLE 5

'H-n.m.r. (CDCl₃) δ=7.64 (1H, broad s), 7.0–7.4 (3H, m), 5.39 (1H, s), 4.70 (2H, s), 4.23 (2H, q, J=7 Hz), 3.58 (3H, s), 3.42 (2H, s), 3.29 (2H, s), 2.27 (3H, s), 1.19 (3H, s) and 1.15 (3H, t, J=7 Hz).

EXAMPLE 13

1-{[4-(2,3-Dichlorophenyl)-3-ethoxycarbonyl-5-methoxycarbonyl-6-methyl-1,4-dihydropyrid-2-yl]methoxy}-2-(2-furyl)-2-hydroxypropane

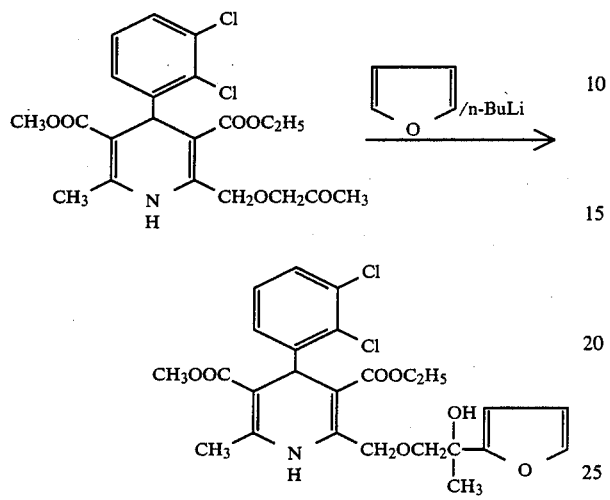

A 1.6M solution of n-butyllithium in hexane (1.4 ml) was added dropwise under nitrogen to a stirred, ice-cooled solution of furan (0.10 ml) in tetrahydrofuran (20 ml). The mixture was stirred with ice-cooling for three hours and then treated over a period of one minute with a solution of 2-{[4-(2,3-dichlorophenyl)-3-ethoxycarbonyl-5-methoxycarbonyl-6-methyl-1,4-dihydropyrid-2-yl]methoxy}acetone (0.50 g) in tetrahydrofuran (20 ml). The mixture was stirred with ice-cooling for 1.5 hours, allowed to warm to room temperature and then quenched with saturated sodium chloride solution. The mixture was extracted twice into ether and the combined ethereal extracts were washed with water, dried over MgSO$_4$ and evaporated. The residue was purified by chromatography on silica (10 g) using hexane plus 50–70% ether as the eluant. Appropriate fractions were combined and evaporated and the residue was crystallised from ether/hexane to give the title compound (0.10 g), m.p. 88°–90° C.

Analysis: Found: C, 57.12; H, 5.17; N, 2.59; $C_{25}H_{27}Cl_2NO_7$ requires: C, 57.26; H, 5.19; N, 2.67.

EXAMPLE 14

1-{[4-(2,3-Dichlorophenyl)-3-ethoxycarbonyl-5-methoxycarbonyl-6-methyl-1,4-dihydropyrid-2-yl]methoxy}-2-hydroxy-2-(2-pyridylmethyl)propane was prepared similarly to the method described in the previous Example using 2-methylpyridine as the starting material instead of furan. In this case the addition of the n-butyllithium and the subsequent reaction of the intermediate 2-lithiomethylpyridine were both carried out with cooling by an acetone/cardice bath. The product was characterised as its hemihydrate, m.p. 163°–164° C.

Analysis %: Found: C, 58.28; H, 5.48; N, 5.23; $C_{27}H_{30}Cl_2N_2O_6.0.5H_2O$ requires: C, 58.07; H, 5.41; N, 5.02.

EXAMPLE 15

1-{[4-(2,3-Dichlorophenyl)-3-ethoxycarbonyl-5-methoxycarbonyl-6-methyl-1,4-dihydropyrid-2-yl]methoxy}-2-hydroxy-2-(2-imidazolyl)propane was prepared similarly to the method described in Example 13 using 1-(diethoxymethyl)imidazole as the starting material instead of furan.

In this case the addition of the n-butyllithium and the subsequent reaction of the intermediate 1-diethoxymethyl-2-lithioimidazole were both performed with cooling by a m-xylene/cardice bath. The product was characterised as a hemihydrate, m.p. 183° C.

Analysis %: Found: C, 53.99; H, 5.24; N, 7.97; $C_{24}H_{27}Cl_2N_3O_6.0.5H_2O$ requires: C, 54.04; H, 5.29; N, 7.88.

EXAMPLE 16

1-{[4-(2,3-Dichlorophenyl)-3-ethoxycarbonyl-5-methoxycarbonyl-6-methyl-1,4-dihydropyrid-2-yl]methoxy}-2,3-dihydroxy-2-methylpropane

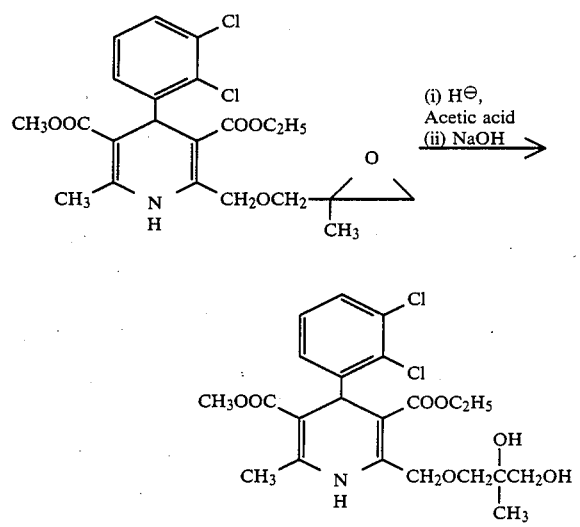

A solution of 2-{[4-(2,3-dichlorophenyl-3-ethoxycarbonyl-5-methoxycarbonyl-6-methyl-1,4-dihydropyrid-2-yl]methoxymethyl}-2-methyloxirane (0.47 g) in acetic acid (20 ml) containing two drops of concentrated sulphuric acid was stirred at room temperature for 4.5 hours and then evaporated. The residue was dissolved in dioxane (10 ml) and the solution treated with 2.5M aqueous sodium hydroxide solution (10 ml). The mixture was stirred at room temperature for four days and evaporated. The residue was taken up in dichloromethane and the solution washed twice with dilute hydrochloric acid, dried over MgSO$_4$ and evaporated. The residue was purified by chromatography on SiO$_2$ (3 g) using dichloromethane plus 30-0% hexane followed by dichloromethane plus 1% methanol as the eluant. Appropriate fractions were combined and evaporated and the residue crystallised from diisopropyl ether to give the title compound (0.10 g), m.p. 135°–138° C.

Analysis %: Found: C, 54.06; H, 5.62; N, 2.63; $C_{22}H_{27}ClNO_7$ requires: C, 54.10; H, 5.57; N, 2.87.

EXAMPLE 17

1-Amino-3-{[4-(2,3-dichlorophenyl)-3-ethoxycarbonyl-5-methoxycarbonyl-6-methyl-1,4-dihydropyrid-2-yl]methoxy}-2-hydroxy-2-methylpropane fumarate

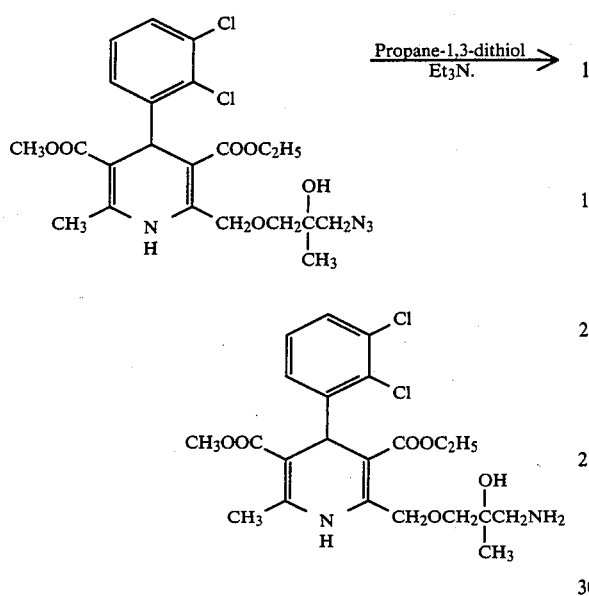

A solution of 1-azido-3-{[4-(2,3-dichlorophenyl)-3-ethoxycarbonyl-5-methoxycarbonyl-6-methyl-1,4-dihydropyrid-2-yl]methoxy}-2-hydroxy-2-methylpropane (1.54 g), propane-1,3-dithiol (1.2 ml) and triethylamine (1.7 ml) in methanol (30 ml) was stirred at room temperature for eight days, filtered and evaporated. The residue was partitioned between ethyl acetate and water and the layers separated. The organic layer was washed with water, dried over $Na_2SO_4$ and evaporated. The residue was purified by chromatography on $SiO_2$ (15 g) using dichloromethane plus 0–40% methanol as the eluant. Appropriate fractions were combined and evaporated. The residue was taken up in ethyl acetate and the solution was treated with excess fumaric acid. The resulting solid was collected, washed with ethyl acetate and dried to give the title compound (0.49 g), m.p. 110°–115° C.

Analysis %: Found: C, 52.01; H, 5.50; N, 4.88; $C_{22}H_{28}Cl_2N_2O_6 \cdot C_4H_4O_4$ requires: C, 51.74; H, 5.31; N, 4.64.

EXAMPLE 18

1-Amino-3-{[4-(2,3-dichlorophenyl)-3-ethoxycarbonyl-5-methoxycarbonyl-6-methyl-1,4-dihydropyrid-2-yl]methoxy}-2-hydroxypropane fumarate hydrate was prepared similarly to the method described in the previous Example using 1-azido-3-{[4-(2,3-dichlorophenyl)-3-ethoxycarbonyl-5-methoxycarbonyl-6-methyl-1,4-dihydropyrid-2-yl]methoxy}-2-hydroxypropane, propane-1,3-dithiol and triethylamine in methanol. The product was characterised as a hydrate of the fumarate salt, m.p. 170° C.

Analysis %: Found: C, 49.66; H, 5.33; N, 5.01; $C_{21}H_{26}Cl_2N_2O_6 \cdot C_4H_4O_4 \cdot H_2O$ requires: C, 49.42; H, 5.27; N, 4.61.

EXAMPLE 19

1-{[4-(2,3-Dichlorophenyl)-3-ethoxycarbonyl-5-methoxycarbonyl-6-methyl-1,4-dihydropyrid-2-yl]methoxy}-2-hydroxy-2-methyl-3-(1,2,4-triazol-4-yl)propane

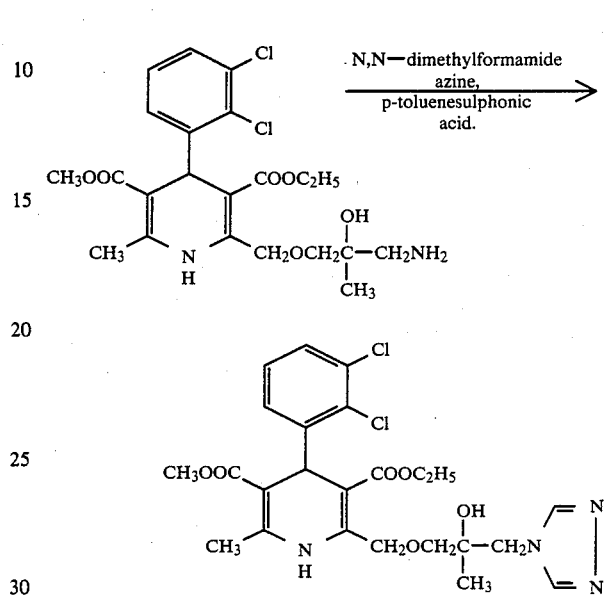

A solution of 1-amino-3-{[4-(2,3-dichlorophenyl)-3-ethoxycarbonyl-5-methoxycarbonyl-6-methyl-1,4-dihydropyrid-2-yl]methoxy}-2-hydroxy-2-methylpropane (0.25 g), N,N-dimethylformamide azine (0.21 g) and para-toluenesulphonic acid (10 mg) in toluene (10 ml) was heated under reflux for 1.5 hours and then partitioned between ethyl acetate and water. The layers were separated and the organic layer was washed with water, dried over $Na_2SO_4$ and evaporated. The residue was purified by chromatography on $SiO_2$ (5 g) using dichloromethane plus 0–5% methanol as the eluant. Appropriate fractions were combined and evaporated and the residue triturated with ether. The resulting solid was collected, washed with ether and dried to give the title compound (0.18 g), m.p. 172°–176° C.

Analysis %: Found: C, 53.15; H, 5.30; N, 10.03; $C_{24}H_{28}Cl_2N_4O_6$ requires: C, 53.43; H, 5.19; N, 10.39.

EXAMPLE 20

1-{[4-(2,3-Dichlorophenyl)-3-ethoxycarbonyl-5-methoxycarbonyl-6-methyl-1,4-dihydropyrid-2-yl]methoxy}-2,3-dihydroxypropane hemihydrate

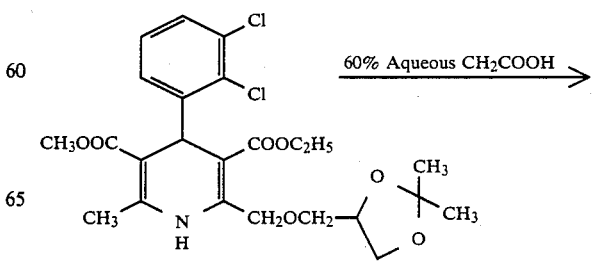

-continued

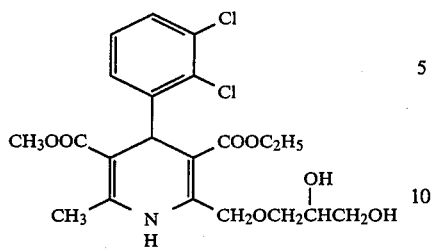

A solution of 4-{[4-(2,3-dichlorophenyl)-3-ethoxycarbonyl-5-methoxycarbonyl-6-methyl-1,4-dihydropyrid-2-yl]methoxymethyl}-2,2-dimethyl-1,3-dioxolane (5.9 g) in 60% aqueous acetic acid was stirred at room temperature for 27 hours and then evaporated. The residue was partitioned between ethyl acetate and water and the organic layer was washed with water, dried over $Na_2SO_4$ and evaporated. The residue was purified by chromatography on $SiO_2$ (60 g) using toluene plus 0–100% ethyl acetate as the eluant. Appropriate fractions were combined and evaporated and the residue crystallised from ether to give the title compound (2.3 g) as a hemihydrate, m.p. 115°–120° C.

Analysis %: Found: C, 52.40; H, 5.29; N, 2.96. $C_{21}H_{25}Cl_2NO_7.0.5H_2O$ requires: C, 52.18; H, 5.42; N, 2.90.

EXAMPLE 21

1-{[4-(2-Chloro-3-trifluoromethylphenyl)-3-ethoxycarbonyl-5-methoxycarbonyl-6-methyl-1,4-dihydropyrid-2-yl]methoxy}-2,3-dihydroxypropane hemihydrate was prepared by the method described in the previous Example 4-{[4-(2-chloro-3-trifluoromethylphenyl)-3-ethoxycarbonyl-5-methoxycarbonyl-6-methyl-1,4-dihydropyrid-2-yl]methoxymethyl}-2,2-dimethyl-1,3-dioxolane and 60% aqueous acetic acid. The product was characterised as a hemihydrate, m.p. 114° C.

Analysis %: Found: C, 51.09; H, 4.91; N, 2.83; $C_{22}H_{25}ClF_3NO_7.0.5H_2O$: C, 51.12; H, 5.07; N, 2.71.

EXAMPLE 22

1-{[4-(2,3-Dichlorophenyl)-3-ethoxycarbonyl-5-methoxycarbonyl-6-methyl-1,4-dihydropyrid-2-yl]methoxy}-2,4-dihydroxybutane

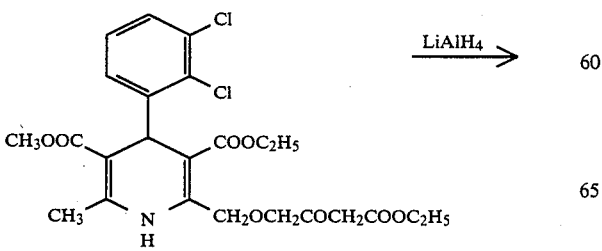

A solution of ethyl 4-{[4-(2,3-dichlorophenyl)-3-ethoxycarbonyl-5-methoxycarbonyl-6-methyl-1,4-dihydropyrid-2-yl]methoxy}acetoacetate (0.99 g) (see European patent application publication no. 0132375) in tetrahydrofuran (10 ml) was added dropwise over five minutes to a stirred, ice-cooled suspension of lithium aluminium hydride (0.19 g) in tetrahydrofuran (20 ml). The ice-cooled mixture was stirred for 40 minutes, quenched into water and partitioned between ethyl acetate and 1M hydrochloric acid. The layers were separated and the organic layer was washed with water, dried over $Na_2SO_4$ and evaporated. The residue was purified by chromatography on $SiO_2$ (8 g) using dichloromethane plus 0–50% ethyl acetate as the eluant. Appropriate fractions were combined and evaporated and the residue triturated with ether/hexane. The resulting solid was collected, washed with ether and dried to give the title compound (0.25 g), m.p. 86°–89° C.

Analysis %: Found: C, 54.38; H, 5.65; N, 3.24; $C_{22}H_{27}Cl_2NO_7$ requires: C, 54.10; H, 5.53; N, 2.87.

EXAMPLE 23

1-{[3,5-Bis(methoxycarbonyl)-4-(2-chlorophenyl)-6-methyl-1,4-dihydropyrid-2-yl]methylthio}-2,3-dihydroxypropane

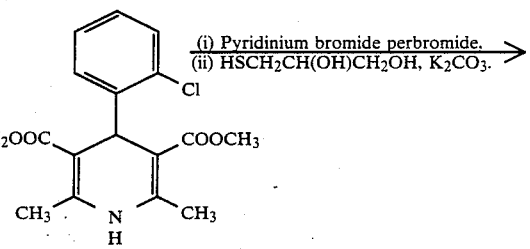

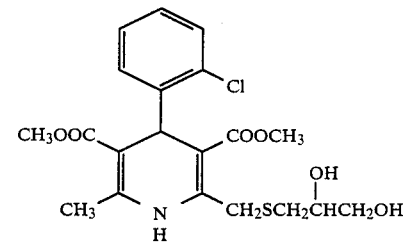

Pyridinium bromide perbromide (2.00 g) was added in one portion to a stirred, ice-cooled solution of 3,5-bis(methoxycarbonyl)-4-(2-chlorophenyl)-2,6-dimethyl-1,4-dihydropyridine (1.68 g) and pyridine (0.8 ml) in dichloromethane (30 ml). The ice-cooled mixture was stirred for 1.5 hours, washed twice with ice-cold 1M hydrochloric acid and once with ice-water, dried over Na₂SO₄ and evaporated without external heating. The residue was dissolved in tetrahydrofuran (10 ml) and the solution was added to a stirred solution of 1-mercapto-2,3-dihydroxypropane (1.08 g) in tetrahydrofuran (20 ml) containing potassium carbonate (1.38 g). The mixture was stirred at room temperature for 16 hours and then partitioned between ethyl acetate and water. The layers were separated and the organic layer was washed with water, dried over Na₂SO₄ and evaporated. The residue was purified by chromatography on SiO₂ (13 g) using dichloromethane plus 0–50% ethyl acetate as eluant. Appropriate fractions were combined and evaporated to give the title compound (0.34 g) as a foam.

Analysis %: Found: C, 53.84; H, 5.53; N, 3.21; $C_{20}H_{24}ClNO_6S$ requires: C, 54.36; H, 5.44; N, 3.17.

The following Preparations describe the preparation of certain starting materials.

Preparation 1

2-{[4-(2,3-Dichlorophenyl)-3-ethoxycarbonyl-5-methoxycarbonyl-6-methyl-1,4-dihydropyrid-2-yl]methoxymethyl}-2-methyloxirane

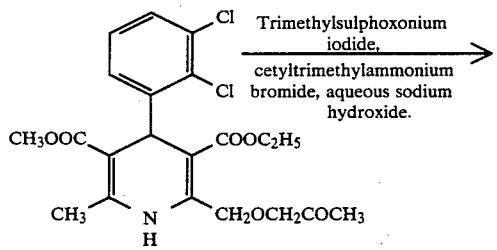

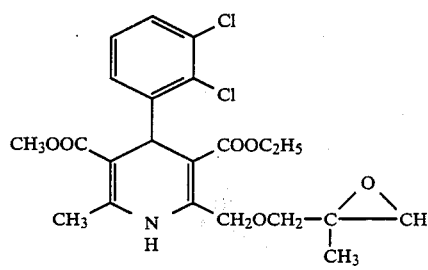

A stirred solution of 2-{[4-(2,3-dichlorophenyl)-3-ethoxycarbonyl-5-methoxycarbonyl-6-methyl-1,4-dihydropyrid-2-yl]methoxy}acetone (0.91 g), trimethylsulphoxonium iodide (0.49 g) and cetyltrimethylammonium bromide (50 mg) in a mixture of 5M aqueous sodium hydroxide solution (15 ml) and 1,1,1-trichloroethane (15 ml) was heated at 60°–65° C. for 1.5 hours. The layers were separated and the aqueous layer extracted twice into dichloromethane. The combined organic layers were washed with water, dried over Na₂SO₄ and evaporated. The residue was purified by chromatography on SiO₂ (13 g) using toluene plus 0–40% ethyl acetate as the eluant. Appropriate fractions were combined and evaporated and the residue triturated with diisopropyl ether. The resulting solid was collected, washed with diisopropyl ether and dried to give the title compound (0.34 g), m.p. 107°–112° C.

Analysis %: Found: C, 56.13; H, 5.35; N, 3.30; $C_{22}H_{25}Cl_2NO_6$ requires: C, 56.17; H, 5.23; N, 2.98.

Preparation 2

2-{[4-(2,3-Dichlorophenyl)-3-ethoxycarbonyl-5-methoxycarbonyl-6-methyl-1,4-dihydropyrid-2-yl]methoxymethyl}oxirane

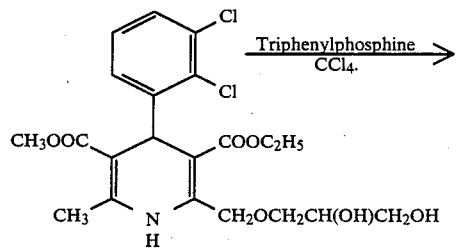

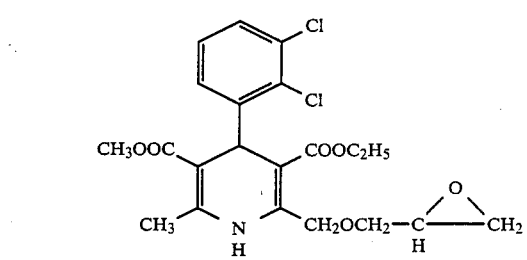

A solution of 1-{[4-(2,3-dichlorophenyl)-3-ethoxycarbonyl-5-methoxycarbonyl-6-methyl-1,4-dihydropyrid-2-yl]methoxy}-2,3-dihydroxypropane (4.74 g) (see Example 20) and triphenylphosphine (2.62 g) in carbon tetrachloride (60 ml) was heated under reflux for 4 hours and then diluted with dichloromethane and water. The layers were separated and the aqueous layer was extracted into dichloromethane. The combined organic layers were washed with water, dried over Na₂SO₄ and evaporated. The residue was purified by chromatography on SiO₂ (80 g) using toluene plus 0–20% ethyl acetate as the eluant. Appropriate fractions were combined and evaporated and the residue triturated with diisopropyl ether. The resulting solid was collected, washed with diisopropyl ether and dried to give the title compound (1.40 g), m.p. 103°–104° C.

Analysis %: Found: C, 55.56; H, 5.09; N, 2.89; $C_{21}H_{23}Cl_2NO_6$ requires: C, 55.26; H, 5.04; N, 3.07.

Preparation 3

4-{[4-(2,3-Dichlorophenyl)-3-ethoxycarbonyl-5-methoxycarbonyl-6-methyl-1,4-dihydropyrid-2-yl]methoxymethyl}-2,2-dimethyl-1,3-dioxolane

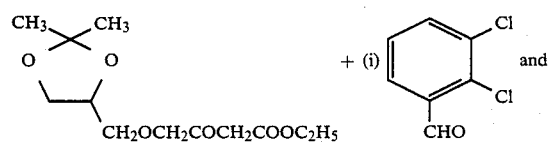

-continued then (ii) CH₃C(NH₂)=CH.CO₂CH₃

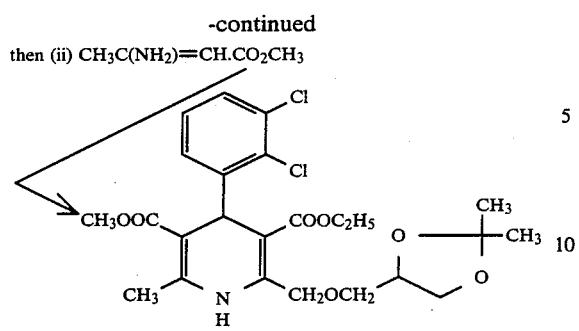

Piperidine (1.0 g) was added dropwise over 5 minutes to a stirred, ice-cooled solution of ethyl 4-{(2,2-dimethyl-1,3-dioxolan-4-yl)methoxy}acetoacetate (26.0 g) (see Preparation 5) and 2,3-dichlorobenzaldehyde (17.5 g) in 2-propanol (200 ml) and the mixture was stirred with ice-cooling for 2 hours and at room temperature for 14 hours. The mixture was evaporated and the residue twice taken up in toluene and evaporated. The residue was purified by chromatography on silica (150 g) using toluene plus 0–40% ethyl acetate as the eluant. Appropriate fractions were combined and evaporated to give essentially pure ethyl 2-(2,3-dichlorobenzylidene)-4-{(2,2-dimethyl-1,3-dioxolan-4-yl)methoxy}acetoacetate (17.3 g) as an oil. A solution of this oil in 2-propanol (150 ml) was treated with methyl 3-aminocrotonate (5.0 g) and the mixture stirred at room temperature for 24 hours. The mixture was evaporated and the residue twice taken up in toluene and evaporated. The residue was purified by chromatography on SiO₂ (110 g) using toluene plus 0–10% ethyl acetate as the eluant. Appropriate fractions were combined and evaporated to give the title compound (2.75 g), m.p. 135°–137° C.

Analysis %: Found: C, 56.02; H, 5.63; N, 2.75; $C_{24}H_{29}Cl_2NO_7$ requires: C, 56.04; H, 5.68; N, 2.72.

Preparation 4

4-{[4-(2-Chloro-3-trifluoromethylphenyl)-3-ethoxycarbonyl-5-methoxycarbonyl-6-methyl-1,4-dihydropyrid-2-yl]methoxymethyl}-2,2-dimethyl-1,3-dioxolane was prepared by the method described in Preparation 3 using 2-chloro-3-trifluoromethylbenzaldehyde instead of 2,3-dichlorobenzaldehyde. The product had a melting point of 124° C.

Analysis %: Found: C, 54.54; H, 5.26; N, 2.61; $C_{25}H_{29}ClF_3NO_7$ requires: C, 54.80; H, 5.33; N, 2.56.

Preparation 5

Ethyl 4-{(2,2-dimethyl-1,3-dioxolan-4-yl)methoxy}acetoacetate

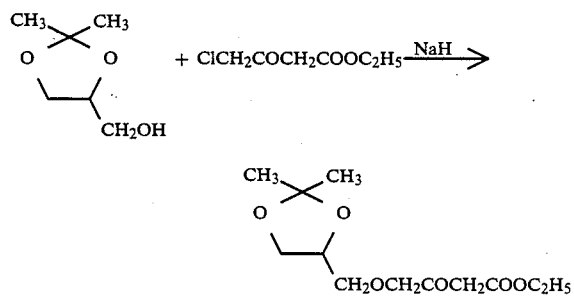

A solution of 2,2-dimethyl-4-hydroxymethyl-1,3-dioxolane (13.2 g) in tetrahydrofuran (50 ml) was added dropwise to a stirred suspension of sodium hydride (8.0 g, 60% dispersion in oil) in tetrahydrofuran (150 ml) and the mixture was then treated dropwise with a solution of ethyl 4-chloroacetoacetate (16.5 g) in tetrahydrofuran (50 ml). The mixture was stirred at room temperature overnight and evaporated. The residue was quenched with 10% aqueous acetic acid and extracted twice into dichloromethane. The combined dichloromethane extracts were washed with saturated brine, dried over MgSO₄ and evaporated. The residue was purified by chromatography on SiO₂ (100 g) using toluene plus 0–20% ethyl acetate as the eluant. Appropriate fractions were combined and evaporated to give the title compound (5.6 g) as an oil. This compound was used in Preparations 3 and 4 without further purification.

Preparation 6

1-{[4-(2,3-Dichlorophenyl)-3-ethoxycarbonyl-5-methoxycarbonyl-6-methyl-1,4-dihydropyrid-2-yl]methoxy}acetone A solution of carbonyl diimidazole (8.00 g) and 2-{[4-(2,3-dichlorophenyl)-3-ethoxycarbonyl-5-methoxycarbonyl-6-methyl-1,4-dihydropyrid-2-yl]methoxy}acetic acid (20.00 g) (see European patent application publication No. 0100189) in dichloromethane (400 ml) was stirred at room temperature under nitrogen for 2 hours and then added to a solution of pyridine (3.60 g) and 2,2-dimethyl-1,3-dioxan-4,6-dione (6.50 g) in dichloromethane over 5 minutes. The mixture was stirred at room temperature for 2 days, washed successively with ice-cooled 2.5M hydrochloric acid and saturated brine, dried over magnesium sulphate and evaporated. The residue was dissolved in water (300 ml) and acetic acid (150 ml) and refluxed for 5 hours. The mixture was evaporated and partitioned between diethyl ether (800 ml) and 10% aqueous sodium carbonate. The ether solution was dried over magnesium sulphate and evaporated. The residue was chromatographed on silica (50 g) using 30% hexane in dichloromethane as the eluant. Fractions which contained the pure product were evaporated to give the title compound (6.5 g), m.p. 117°–119°.

Analysis %: Found: C, 55.41; H, 5.17; N, 3.46; $C_{21}H_{23}Cl_2NO_6$ requires: C, 55.27; H, 5.08; N, 3.07.

Preparation 7

1-{[4-(2,3-Dichlorophenyl)-3-ethoxycarbonyl-5-methoxycarbonyl-6-methyl-1,4-dihydropyrid-2-yl]methoxy}acetone

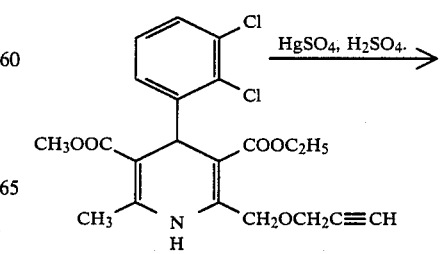

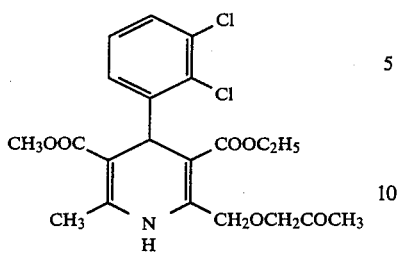

A solution of 1-{[4-(2,3-dichlorophenyl)-3-ethoxycarbonyl-5-methoxycarbonyl-6-methyl-1,4-dihydropyrid-2-yl]methoxy}-2-propyne (1.06 g) [see Preparation 8], mercuric sulphate (0.10 g) and concentrated sulphuric acid (0.2 ml) in a mixture of water (20 ml) and dioxane (20 ml) was heated at 60° for 2 hours and then evaporated. The residue was partitioned between ether and water and the organic layer washed with saturated aqueous sodium chloride solution and water, dried over sodium sulphate and evaporated to give the title compound (0.93 g), m.p. 119°–121°. This material was confirmed spectroscopically to be identical to the product of Preparation 6.

Preparation 8

1-{[4-(2,3-Dichlorophenyl)-3-ethoxycarbonyl-5-methoxycarbonyl-6-methyl-1,4-dihydropyrid-2-yl]methoxy}-2-propyne

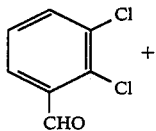

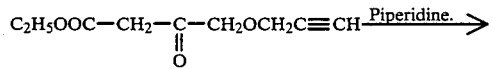

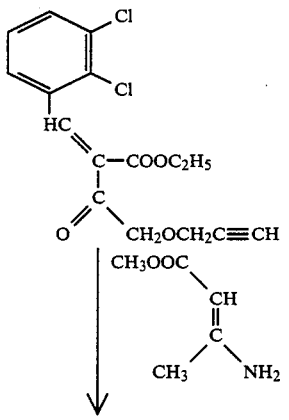

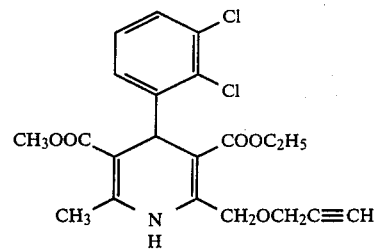

Piperidine (2.4 g) was added dropwise over 10 minutes to a stirred mixture of ethyl 4-(prop-2-ynoxy)acetoacetate (63 g) (see Preparation 9) and 2,3-dichlorobenzaldehyde (60 g) in isopropanol (600 ml) and the mixture was stirred at room temperature for 24 hours. The mixture was then treated with methyl 3-aminocrotonate (39 g), stirred at room temperature for four days and evaporated. The residual oil was dissolved in methanol (300 ml) and the solution kept at −20° for two days. The resulting solid was collected, washed with cold methanol and dried to give the title compound (29.5 g), m.p. 104°–105°, which was used directly.

Preparation 9

Ethyl 4-(prop-2-ynoxy)acetoacetate

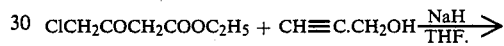

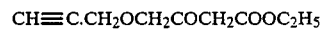

A solution of ethyl 4-chloroacetoacetate (294 g) in tetrahydrofuran (200 ml) was added over 3 hours to a stirred, ice-cooled suspension of sodium hydride (150 g of a 80% dispersion in mineral oil) in tetrahydrofuran (500 ml) at such a rate than the reaction temperature remained ≦20°. A solution of prop-2-ynol (100 g) in tetrahydrofuran (200 ml) was then added over 2 hours to the above mixture with stirring and ice-cooling at such a rate that the reaction temperature never exceeded +25°. The mixture was then stirred at room temperature for 16 hours, poured into 2M HCl (900 ml) and the layers separated. The organic layer was evaporated and the resulting red oil was separated in a separating funnel from the mineral oil. The red oil was taken up in dichloromethane and the resulting solution was washed several times with water, dried over $Na_2SO_4$ and evaporated to give the title compound (313 g) as a dark oil which was used directly in Preparation 8.

Preparation 10

1-{4-[2,3-Dichlorophenyl)-3-ethoxycarbonyl-5-methoxycarbonyl-6-methyl-1,4-dihydropyrid-2-yl]methoxy-}acetone Carbonyl diimidazole (0.81 g) was added to a solution of 2-{[4-(2,3-dichlorophenyl)-3-ethoxycarbonyl-5-methoxycarbonyl-6-methyl-1,4-dihydropyrid-2-yl]methoxy}acetic acid acid (2.30 g) (see European patent application No. 00100189) in tetrahydrofuran (40 ml) and the mixture was stirred at room temperature for 1.25 hours. The solution was then cooled in an acetone/cardice bath and treated dropwise over ten minutes with a 3M solution of methylmagnesium bromide in ether (5.8 ml). The mixture was allowed to warm up slowly to room temperature, stirred at room temperature for two hours, quenched with saturated aqueous ammonium chloride solution and evaporated. The residue was partitioned between chloroform and water and the aqueous layer extracted into chloroform. The combined organic layers were dried over $MgSO_4$ and evaporated. The residue was purified by chromatography on $SiO_2$ (10 g) using dichloromethane plus 40-0% hexane as eluant. Appropriate fractions were combined and evaporated and the residue crystallised from ether to give the title compound (0.16 g), m.p. 117°–119° C. The product was confirmed spectroscopically to be identical to the product of Preparations 6 and 7.

We claim:

1. A compound of the formula:

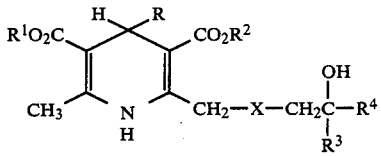

or a pharmaceutically acceptable acid addition salt thereof wherein

R is selected from the group consisting of 2-chlorophenyl, 2,3-dichlorophenyl and 2-chloro-3-trifluoromethylphenyl;

$R^1$ and $R^2$ are each independently $C_1$–$C_4$ alkyl; X is O or S; $R^3$ is H or $C_1$–$C_4$ alkyl; and $R^4$ is selected from the group consisting of 1,2,4-triazol-1-ylmethyl, imidazol-1-ylmethyl, azidomethyl, 2,4,5-trimethylimidazol-1-ylmethyl, 3,4-dihydro-4-oxopyrimidin-2-ylthiomethyl, pyrimidin-2-ylthiomethyl, pyrimidin-2-ylaminomethyl, 3,4-dihydro-4-oxopyrimidin-2-ylaminomethyl, 2-aminopyrimidin-4-yloxymethyl, methoxymethyl, 2-furyl, 2-pyridylmethyl, imidazol-2-yl, hydroxymethyl, aminomethyl, 1,2,4-triazol-4-ylmethyl or 2-hydroxyethyl.

2. A compound of claim 1, wherein $R^1$ and $R^2$ are each independently $C_1$–$C_4$ alkyl, $R^3$ is hydrogen, $R^4$ is hydroxymethyl and X is O.

3. The compound of claim 2, wherein R is 2,3-dichlorophenyl, $R^1$ is methyl and $R^2$ is ethyl.

4. The compound of claim 2, wherein R is 2-chloro-3-trifluorometylphenyl, $R^1$ is methyl and $R^2$ is ethyl.

5. A pharmaceutical composition comprising an antiischaemic or antihypertensive effective amount of a compound according to claim 1 and a pharmaceutically acceptable carrier or diluent.

6. A method of treating hypertension in a mammal which comprises administering to said mammal an antihypertensive effective amount of a compound according to claim 1.

7. A method of treating ischaemia in a mammal which comprises administering to said mammal an anti-ischaemic effective amount of a compound according to claim 1.

* * * * *